(12) United States Patent
Sakai et al.

(10) Patent No.: US 12,207,971 B2
(45) Date of Patent: Jan. 28, 2025

(54) ULTRASOUND DIAGNOSTIC APPARATUS, METHOD FOR CONTROLLING ULTRASOUND DIAGNOSTIC APPARATUS, AND CONTROL PROGRAM OF ULTRASOUND DIAGNOSTIC APPARATUS

(71) Applicant: Konica Minolta, Inc., Tokyo (JP)

(72) Inventors: Takashi Sakai, Yokohama (JP); Toshio Oka, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 139 days.

(21) Appl. No.: 18/309,495

(22) Filed: Apr. 28, 2023

(65) Prior Publication Data

US 2023/0363737 A1 Nov. 16, 2023

(30) Foreign Application Priority Data

May 10, 2022 (JP) .................... 2022-077760

(51) Int. Cl.
*A61B 8/00* (2006.01)
*A61B 8/14* (2006.01)

(52) U.S. Cl.
CPC .............. *A61B 8/461* (2013.01); *A61B 8/14* (2013.01)

(58) Field of Classification Search
CPC ........... A61B 8/461; A61B 8/14; A61B 8/468; A61B 8/467
See application file for complete search history.

(56) References Cited

U.S. PATENT DOCUMENTS

| | | | | |
|---|---|---|---|---|
| 6,254,540 | B1* | 7/2001 | Kikuchi | G01S 15/8993 600/443 |
| 8,519,998 | B2* | 8/2013 | Hashimoto | A61B 8/461 345/589 |
| 2005/0203417 | A1* | 9/2005 | Okuno | A61B 8/5238 600/463 |
| 2006/0112033 | A1* | 5/2006 | Vion | G06N 20/00 706/16 |
| 2006/0184028 | A1* | 8/2006 | Wen | G01S 15/8988 600/441 |

(Continued)

FOREIGN PATENT DOCUMENTS

JP H10-108864 A 4/1998

*Primary Examiner* — Sanjay Cattungal
(74) *Attorney, Agent, or Firm* — LUCAS & MERCANTI, LLP

(57) ABSTRACT

An ultrasound diagnostic apparatus includes: an ultrasound probe that transmits an ultrasound wave and receives a reflected wave; a display that displays an ultrasound image on a screen; and a hardware processor that activates a screen saver processing of displaying an image hiding information displayed on the screen or a freeze processing of stopping transmission and reception of the ultrasound wave when conditions (A1) or (A2) is continuously satisfied for a predetermined time or more while the ultrasound image is displayed, wherein the conditions (A1) and (A2) are: (A1) a state in which, in an input captured image, a change amount of the probe and surroundings is a first threshold or less; and (A2) a state in which a volume of input voice is a second threshold or less, or a state in which a volume of a specific frequency of input sound is a third threshold or less.

19 Claims, 5 Drawing Sheets

(56) References Cited

U.S. PATENT DOCUMENTS

| | | | |
|---|---|---|---|
| 2006/0241428 A1* | 10/2006 | Kao | A61B 8/465 600/437 |
| 2007/0014446 A1* | 1/2007 | Sumanaweera | G06T 15/08 382/128 |
| 2007/0167754 A1* | 7/2007 | Okuno | A61B 8/463 600/437 |
| 2008/0194960 A1* | 8/2008 | Randall | A61B 8/4411 600/459 |
| 2008/0194961 A1* | 8/2008 | Randall | G01S 7/52017 600/459 |
| 2008/0194962 A1* | 8/2008 | Randall | A61B 8/4411 73/40.7 |
| 2008/0194963 A1* | 8/2008 | Randall | A61B 8/00 600/459 |
| 2008/0194964 A1* | 8/2008 | Randall | A61B 8/4411 600/459 |
| 2009/0124907 A1* | 5/2009 | Bruce | A61B 5/7264 600/458 |
| 2010/0022880 A1* | 1/2010 | Sathyanarayana | A61B 5/02007 600/443 |
| 2010/0056924 A1* | 3/2010 | Powers | A61B 8/0816 600/458 |
| 2010/0099988 A1* | 4/2010 | Kurita | G01S 7/52084 600/443 |
| 2011/0162673 A1* | 7/2011 | Samain | A45D 44/005 424/59 |
| 2012/0128218 A1* | 5/2012 | Amyot | G06T 19/00 382/128 |
| 2012/0245465 A1* | 9/2012 | Hansegard | A61B 8/466 600/443 |
| 2013/0182926 A1* | 7/2013 | Lee | G06V 20/20 382/131 |
| 2014/0073925 A1* | 3/2014 | Kho | A61B 8/0866 600/443 |
| 2014/0114194 A1* | 4/2014 | Kanayama | G16H 50/20 600/459 |
| 2014/0144240 A1* | 5/2014 | Barlow | B06B 1/0215 73/632 |
| 2014/0301159 A1* | 10/2014 | Chang | G01S 7/5205 367/7 |
| 2015/0196273 A1* | 7/2015 | Yamamoto | G01S 7/52047 600/447 |
| 2015/0245821 A1* | 9/2015 | Kang | A61B 8/4455 600/459 |
| 2015/0245823 A1* | 9/2015 | Jin | A61B 8/14 600/443 |
| 2015/0265253 A1* | 9/2015 | Kim | A61B 8/4281 600/443 |
| 2015/0320389 A1* | 11/2015 | Miyagi | A61B 8/4427 600/459 |
| 2019/0142374 A1* | 5/2019 | Kruecker | A61B 8/12 600/462 |
| 2021/0052250 A1* | 2/2021 | Sandrin | A61B 8/4444 |
| 2022/0125409 A1* | 4/2022 | Hattori | A61B 8/465 |
| 2022/0133281 A1* | 5/2022 | Hattori | A61B 8/463 600/440 |
| 2022/0142616 A1* | 5/2022 | Murakami | A61B 8/54 |
| 2022/0378401 A1* | 12/2022 | Heid | A61B 8/4444 |
| 2023/0301626 A1* | 9/2023 | Howell | A61B 8/4254 |
| 2024/0315668 A1* | 9/2024 | Tsubota | A61B 8/56 |

* cited by examiner

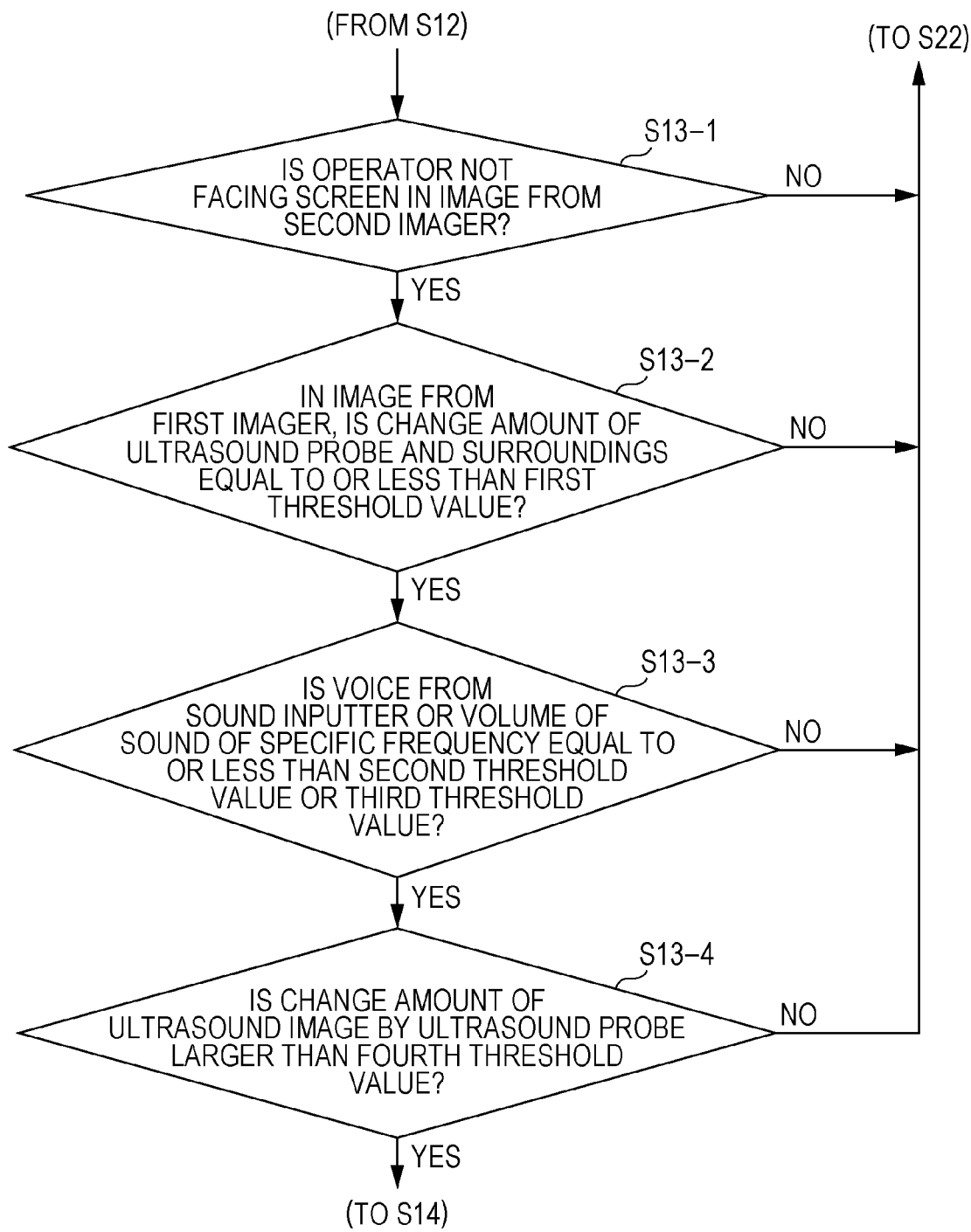

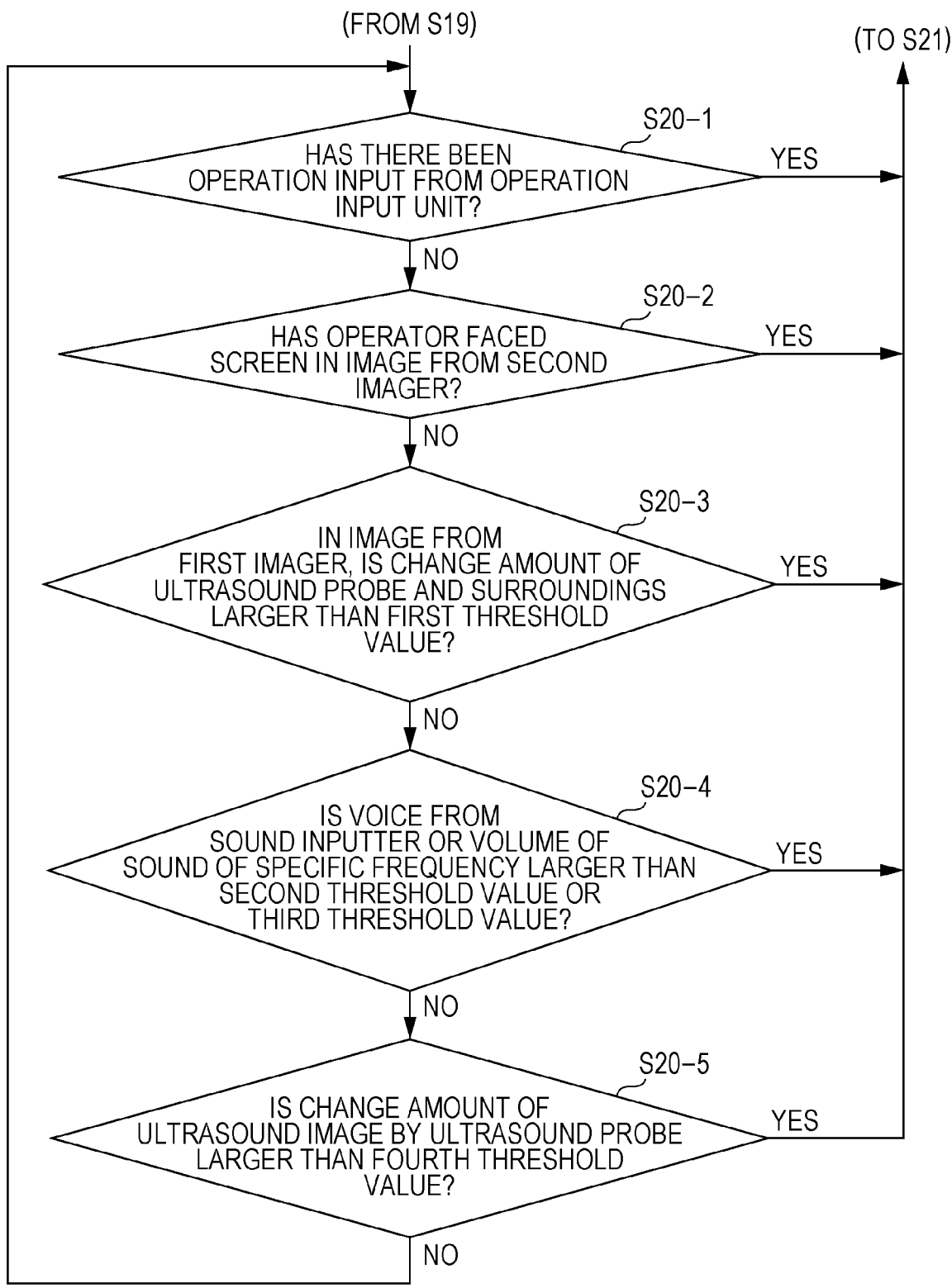

ULTRASOUND DIAGNOSTIC APPARATUS, METHOD FOR CONTROLLING ULTRASOUND DIAGNOSTIC APPARATUS, AND CONTROL PROGRAM OF ULTRASOUND DIAGNOSTIC APPARATUS

The entire disclosure of Japanese patent Application No. 2022-077760, filed on May 10, 2022, is incorporated herein by reference in its entirety.

BACKGROUND

Technological Field

The present invention relates to an ultrasound diagnostic apparatus, a method for controlling an ultrasound diagnostic apparatus, and a control program of an ultrasound diagnostic apparatus.

Description of the Related Art

There is known an ultrasound diagnostic apparatus that transmits and receives ultrasound waves to and from a subject such as a living body using an ultrasound probe, generates an ultrasound image based on a signal obtained from a received ultrasound echo (reflected wave), and displays the generated ultrasound image on a monitor screen.

As an example of the ultrasound diagnostic apparatus described above, there is an ultrasound diagnostic apparatus having a screen saver function and an automatic freeze function for preventing burning of a monitor screen or deterioration of an ultrasound probe as disclosed in JP H10-108864A.

With the screen saver function, it is possible to prevent the ultrasound image from being displayed on the monitor screen for a long time and to prevent burning of the monitor screen. In addition, the screen saver function makes it possible to hide information displayed on the monitor screen, for example, personal information of a patient who is a subject. In addition, the automatic freeze function can prevent power from being continuously supplied to the ultrasound probe for a long time, preventing deterioration of the ultrasound probe.

The above-described screen saver function and automatic freeze function are automatically activated when any one of the following conditions (1) to (3) is satisfied. (1) A non-operation time of a physical input device, for example, a button, a touch panel, a mouse, and the like passes a predetermined time. (2) A predetermined time during which the line of sight of the operator captured by the camera of the ultrasound diagnostic apparatus is not directed to the monitor screen passes (also referred to as a screen attention function). (3) A non-input time of the video to the ultrasound diagnostic apparatus passes for a predetermined time (also referred to as non-signal power save).

For example, in a case where the doctor (operator) moves away from the front of the ultrasound diagnostic apparatus and moves to another examination room, if any one of the above conditions (1) to (3) is satisfied, the above-described screen saver function and automatic freeze function are activated. This makes it possible to prevent image burning on the monitor screen and deterioration of the ultrasound probe, and to hide patient's personal information and the like.

Meanwhile, in the ultrasound diagnostic apparatus, in a case where a doctor performs puncture on a diagnosis site of a patient, there is a case where a needle to be punctured is positioned without moving the ultrasound probe. In this case, since the doctor performs puncture without operating the input device or directing the line of sight to the monitor screen, any one of the above conditions (1) to (3) may be satisfied. Therefore, contrary to the intention of the doctor, the above-described screen saver function and automatic freeze function are activated, and there is a problem that the ultrasound image cannot be checked when it is desired to check the ultrasound image.

SUMMARY

An object of the present invention is to provide an ultrasound diagnostic apparatus, a method for controlling an ultrasound diagnostic apparatus, and a control program of an ultrasound diagnostic apparatus capable of preventing a screen saver function and an automatic freeze function from being activated against an operator's intention.

To achieve the abovementioned object, according to an aspect of the present invention, an ultrasound diagnostic apparatus reflecting one aspect of the present invention comprises: an ultrasound probe that transmits an ultrasound wave and receives a reflected wave of the ultrasound wave; a display that displays an ultrasound image based on the reflected wave on a screen; and a hardware processor that activates at least one of a screen saver processing of displaying, on the screen, a predetermined image hiding information displayed on the screen and a freeze processing of stopping transmission and reception of the ultrasound wave by the ultrasound probe in a case where at least one of following non-operation determination conditions (A1) and (A2) is continuously satisfied for a predetermined time or more while the ultrasound image is displayed on the screen, wherein the non-operation determination conditions (A1) and (A2) are: (A1) a state in which, in an input captured image, a change amount of the ultrasound probe and surroundings of the ultrasound probe is equal to or less than a first threshold value; and (A2) a state in which a volume of input voice is equal to or less than a second threshold value, or a state in which a volume of a specific frequency of input sound is equal to or less than a third threshold value.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 4 is a flowchart illustrating determination of a counting continuation condition of a timer in the flowchart illustrated in FIG. 3; and FIG. 5 is a flowchart illustrating determination of an end condition of an activated function in the flowchart illustrated in FIG. 3.

DETAILED DESCRIPTION OF EMBODIMENTS

Hereinafter, one or more embodiments of the present invention will be described with reference to the drawings. However, the scope of the invention is not limited to the disclosed embodiments.

[Ultrasound Diagnostic Apparatus]

Figure 1:
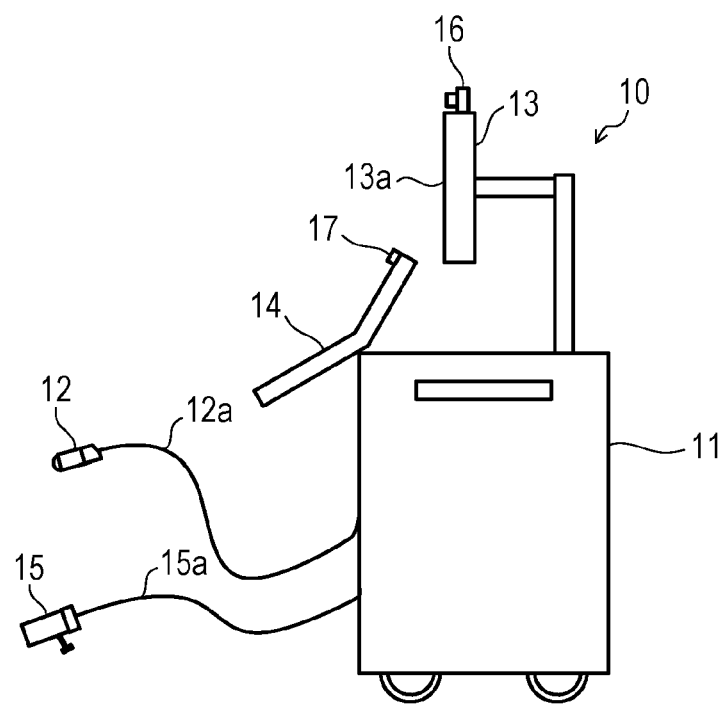
FIG. 1 is a view illustrating an appearance of an ultrasound diagnostic apparatus according to an embodiment of the present invention.
Figure 2:
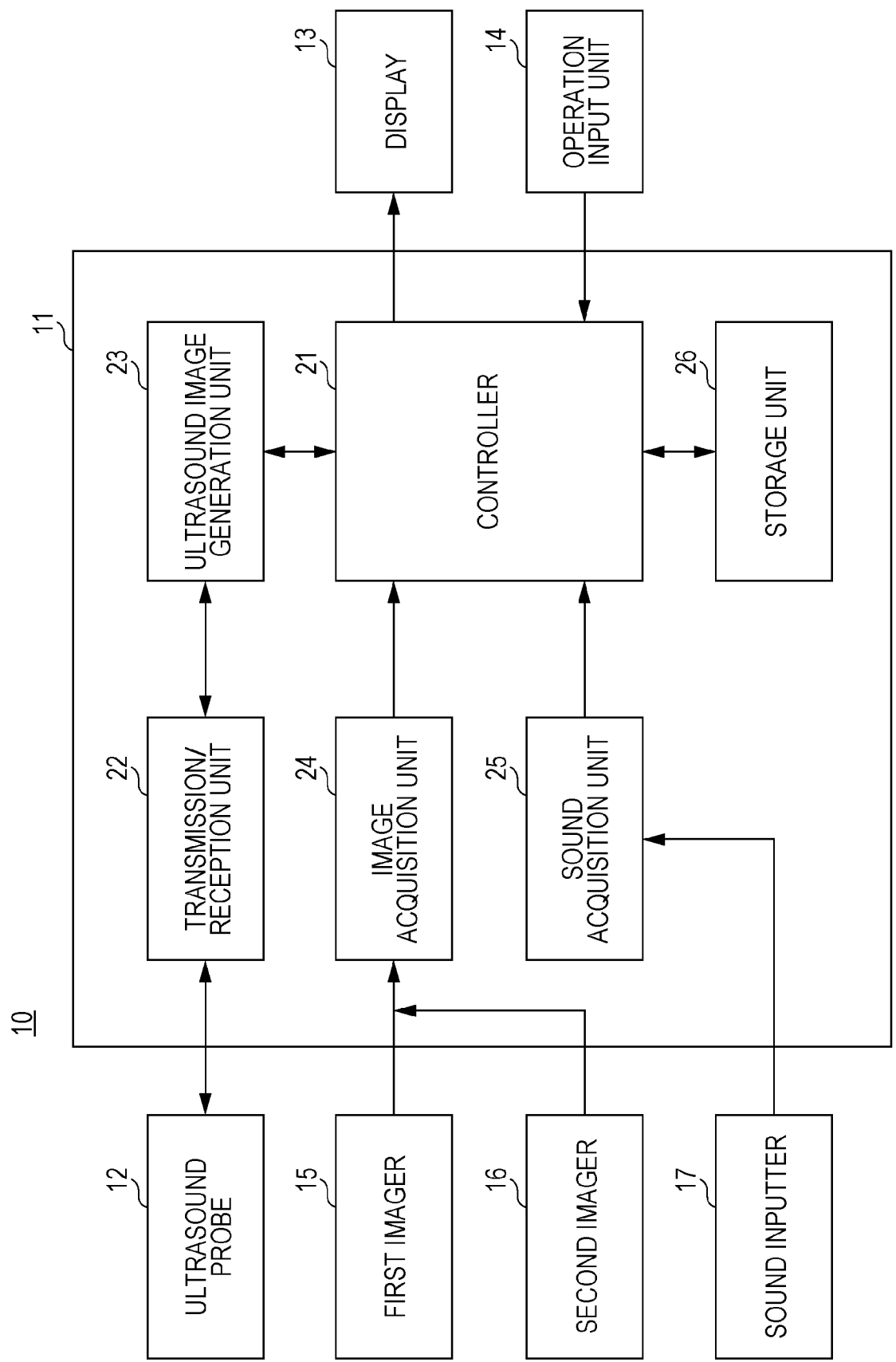
FIG. 2 is a block diagram illustrating main parts of the ultrasound diagnostic apparatus illustrated in FIG. 1.

An ultrasound diagnostic apparatus according to the present embodiment will be described with reference to FIGS. 1 and 2. FIG. 1 is a view illustrating an appearance of an ultrasound diagnostic apparatus 10. In addition, FIG. 2 is a block diagram illustrating main parts of the ultrasound diagnostic apparatus 10.

The ultrasound diagnostic apparatus 10 is used to visualize the shape, property, or dynamics of a living tissue inside a subject such as a living body as an ultrasound image and perform image diagnosis.

The ultrasound diagnostic apparatus 10 includes an apparatus body 11, an ultrasound probe 12, a display 13, an operation input unit 14, a first imager 15, a second imager 16, a sound inputter 17, and the like. In the ultrasound diagnostic apparatus 10, the ultrasound probe 12 and the first imager 15 are connected to the apparatus body 11 via cables 12a and 15a, respectively. Note that the ultrasound probe 12 and the first imager 15 may be connected to the apparatus body 11 via wireless communication.

The ultrasound probe 12 functions as an acoustic sensor that transmits an ultrasound beam into the subject, receives an ultrasound echo (reflected wave) reflected in the subject out of the transmitted ultrasound beam, and converts the ultrasound echo into an electrical signal.

The ultrasound probe 12 includes, for example, a transducer array (for example, a piezoelectric transducer array) disposed in an array, a channel switching unit (for example, a multiplexer) that performs switching control of a drive state (on or off) of each transducer in the transducer array individually or in units of blocks, and the like.

In the ultrasound probe 12, each transducer converts a voltage pulse transmitted from a transmission/reception unit 22 of the apparatus body 11 into an ultrasound beam and transmits the ultrasound beam into the subject, and receives an ultrasound echo reflected in the subject and converts the ultrasound echo into an electrical signal. In the ultrasound probe 12, the channel switching unit sequentially switches the transducers to be driven along the scanning direction to scan the subject with ultrasound waves.

Then, the electrical signal of the ultrasound echo converted by the ultrasound probe 12 is transmitted to the transmission/reception unit 22 via the cable 12a and input to an ultrasound image generation unit 23. The ultrasound image generation unit 23 generates an ultrasound image based on the input electrical signal of the ultrasound echo, and the generated ultrasound image is input to a controller 21. The ultrasound images are generated in time series, and the time-series ultrasound images input to the controller 21 are stored in a storage unit 26 or displayed on the display 13, for example.

An operator who operates the ultrasound diagnostic apparatus 10, for example, a medical worker such as a doctor or a medical technician, uses the ultrasound probe 12 connected to the apparatus body 11 by the cable 12a, and brings the ultrasound transmission/reception surface into contact with the surface (skin) of the subject to acquire an ultrasound image in the subject.

As the ultrasound probe 12, various types of ultrasound probes can be used. For example, here, a type in which the ultrasound transmission/reception surface of the ultrasound probe 12 is brought into contact with the surface of the subject is used, but an ultrasound probe and the like that acquires an ultrasound image by inserting the ultrasound transmission/reception unit into a body cavity and the like of the subject may be used.

The display 13 displays information such as an ultrasound image generated by the controller 21. As the display 13, for example, a liquid crystal display, an organic EL display, a CRT display, a touch panel display, and the like can be used.

The operation input unit 14 is a user interface for the operator to perform an input operation, converts the input operation performed by the operator into an operation signal, and inputs the operation signal to the controller 21. The operation input unit 14 includes, for example, an operation panel having a plurality of operation buttons, a keyboard, a mouse, and the like. In a case where a touch panel display is used as the display 13, the touch panel portion functions as a part of the operation input unit 14.

In the operation input unit 14, the operator performs input operations such as selecting an operation mode of the ultrasound diagnostic apparatus 10 and selecting information to be displayed on the display 13.

The first imager 15 is, for example, a digital camera having an optical system such as a lens or an imaging element, and images an imaging range with the imaging element to generate a captured image. The first imager 15 continuously generates captured images, and the captured images generated continuously (in time series) are transmitted to an image acquisition unit 24 of the apparatus body 11 via the cable 15a and input to the controller 21. The time-series captured images input to the controller 21 are subjected to predetermined processing, and are stored in the storage unit 26 or displayed on the display 13, for example.

Since the first imager 15 images the ultrasound probe 12 and the site of the subject of the surroundings in time series, the captured images may be stored in the storage unit 26 in synchronization with time-series ultrasound images obtained using the ultrasound probe 12 and the like.

The first imager 15 is connected to the apparatus body 11 via the cable 15a, and the position and orientation of the first imager 15 can be changed as appropriate. In particular, the first imager 15 is disposed in a manner that the ultrasound probe 12 and the site of the subject of the surroundings can be imaged, for example, a pressing state (a state such as a position and a posture) of the ultrasound probe 12 against the portion of the site can be grasped.

Similarly to the first imager 15, the second imager 16 is, for example, a digital camera having an optical system such as a lens or an imaging element, and images an imaging range with the imaging element to generate a captured image. The second imager 16 also continuously generates captured images, and the captured images generated continuously (in time series) are transmitted to the image acquisition unit 24 of the apparatus body 11 and input to the controller 21. The time-series captured images input to the controller 21 are subjected to predetermined processing and stored in the storage unit 26, for example.

The second imager 16 is disposed, for example, on the upper part of the display 13, and is basically configured to be able to image a predetermined range in front of a screen 13a. In particular, the second imager 16 is disposed in a manner that the operator facing the screen 13a of the display 13 can be imaged.

Note that, here, as an example, the ultrasound probe 12, the first imager 15 for subject imaging, and the second imager 16 for operator imaging are separately provided. The present invention is not limited to such a configuration, and for example, as long as the imaging range is wide, the ultrasound probe 12, the subject, and the operator may be imaged by one imager.

In addition, the first imager 15 and the second imager 16 are not limited to those included in the ultrasound diagnostic apparatus 10, and may be retrofitted to the ultrasound diagnostic apparatus 10. In this case, the first imager 15 and the second imager 16 desirably include, for example, a configuration in which the positions and orientations of the first imager 15 and the second imager 16 can be adjusted, for example, an arm and the like that can be flexibly deformed.

The sound inputter 17 is, for example, a digital microphone, and acquires surrounding sound to generate sound data. The sound data generated by the sound inputter 17 is transmitted to a sound acquisition unit 25 of the apparatus body 11 and input to the controller 21. The sound data input to the controller 21 are subjected to predetermined processing and stored in the storage unit 26, for example.

The sound data acquired by the sound inputter 17 and stored in the storage unit 26 may also be stored in the storage unit 26 in synchronization with a time-series ultrasound image obtained using the ultrasound probe 12 and the like and stored in the storage unit 26 similarly to the captured image captured by the first imager 15.

The sound inputter 17 is disposed in the operation input unit 14, for example, and is basically configured to be able to acquire the voice of the operator who operates the operation input unit 14. Therefore, the sound inputter 17 itself may have directivity, or a filter of a specific frequency for extracting voice from the sound acquired by the sound inputter 17 may be provided.

Note that, here, as an example, the sound inputter 17 is disposed in the operation input unit 14. However, as long as the operator's voice can be acquired, the sound inputter 17 may be provided in the apparatus body 11 or the display 13, or may be wirelessly attached to the operator.

The apparatus body 11 includes the controller 21, the transmission/reception unit 22, the ultrasound image generation unit 23, the image acquisition unit 24, the sound acquisition unit 25, the storage unit 26, and the like.

The transmission/reception unit 22 is a drive circuit of the ultrasound probe 12, transmits a voltage pulse as a drive signal to each transducer of the ultrasound probe 12, and receives an electrical signal of an ultrasound echo generated by being received by each transducer of the ultrasound probe 12. The electrical signal of the ultrasound echo received by the transmission/reception unit 22 is input to the ultrasound image generation unit 23.

Based on the electrical signal of the ultrasound echo input from the transmission/reception unit 22, specifically, the ultrasound image generation unit 23 performs predetermined signal processing on the electrical signal of the ultrasound echo to generate an ultrasound image. At this time, the ultrasound image generation unit 23 generates time-series ultrasound images at a frame rate corresponding to the scanning speed of the ultrasound probe 12. Note that the predetermined signal processing for generating the ultrasound image from the electrical signal of the ultrasound echo may be performed using known signal processing, and the detailed description will be omitted here.

The ultrasound image generated by the ultrasound image generation unit 23 is input to the controller 21, and the controller 21 stores the generated ultrasound image in the storage unit 26 or displays the generated ultrasound image on the display 13, for example.

The image acquisition unit 24 acquires captured images generated by the first imager 15 and the second imager 16. The image acquisition unit 24 acquires captured images in time series at intervals of frame rates at which the first imager 15 and the second imager 16 generate captured images, for example. The captured images acquired by the image acquisition unit 24 are input to the controller 21.

The sound acquisition unit 25 acquires sound data generated by the sound inputter 17. The sound data acquired by the sound acquisition unit 25 is input to the controller 21.

The storage unit 26 is, for example, a storage device such as a hard disk drive (HDD), a solid state drive (SSD), or a flash memory. The storage unit 26 stores the above-described ultrasound image, captured image, sound data, and the like.

The controller 21 is, for example, a computer including a central processing unit (CPU), a read only memory (ROM), a random access memory (RAM), and the like. The controller 21 also includes a timer to be described later. The timer may count down or count up.

The controller 21 acquires an operation signal of the operator from the operation input unit 14, controls the operation of each unit of the ultrasound diagnostic apparatus 10 based on the operation signal, and performs processing of the input ultrasound image, captured image, sound data, and the like.

For example, the controller 21 stores the ultrasound image input from the ultrasound image generation unit 23 in the storage unit 26 or displays the ultrasound image on the display 13 according to the operation mode of the ultrasound diagnostic apparatus 10. In addition, the controller 21 stores the captured image input from the image acquisition unit 24 in the storage unit 26, displays the captured image on the display 13, or performs predetermined image processing described later. In addition, the controller 21 stores the sound data input from the sound acquisition unit 25 in the storage unit 26 or performs predetermined data processing described later.

Here, the CPU performs arithmetic processing according to the program to perform image processing and data processing of an ultrasound image, a captured image, sound data, and the like. Note that part or all of the image processing and the data processing may be performed by a digital arithmetic circuit including a digital signal processor (DSP). Similarly, some or all of the image processing and the data processing may be performed by a dedicated hardware circuit such as an application specific integrated circuit (ASIC) or a field programmable gate array (FPGA).

The controller 21 displays the ultrasound image and the captured image on the display 13, but changes the display form of the ultrasound image and the captured image displayed on the display 13 according to the operation mode of the ultrasound diagnostic apparatus 10.

Here, an operation mode of the ultrasound diagnostic apparatus 10 will be described. Examples of the operation mode of the ultrasound diagnostic apparatus 10 include a live mode, a freeze mode, a moving image reproduction mode, a still image reproduction mode, and the like. The operator inputs an operation signal from the operation input unit 14 to select an operation mode.

The live mode is a mode in which an ultrasound image is acquired using the ultrasound probe 12 and the like, a captured image is acquired by the second imager 16, and the acquired ultrasound image and captured image are displayed on the display 13 in real time. At this time, in a case where the operator performs an image saving operation, a moving image of an ultrasound image or a captured image is recorded in the storage unit 26.

The freeze mode is a mode in which transmission and reception of an ultrasound wave in the ultrasound probe 12 is stopped by the freeze operation of the operator during the live mode, the currently displayed ultrasound image or captured image is displayed as a still image, and real-time display of the ultrasound image or captured image is stopped. At this time, in a case where the operator performs an image saving operation, a still image of an ultrasound image or a captured image is recorded in the storage unit 26.

The moving image reproduction mode is a mode in which a moving image of an ultrasound image or a captured image generated at the time of past ultrasound inspection is read from the storage unit 26 and displayed (reproduced) on the display 13. For example, as described above, during the live mode, the moving image of the ultrasound image or the captured image stored by the image saving operation of the operator is read from the storage unit 26 and displayed on the display 13. In addition, in a case where the operator performs an image saving operation during the moving image reproduction mode, the ultrasound image or the captured image displayed on the display 13 may be recorded in the storage unit 26 as a still image.

The still image reproduction mode is a mode in which a still image of an ultrasound image or a captured image generated at the time of past ultrasound inspection is read from the storage unit 26 and displayed (reproduced) on the display 13. For example, as described above, during the freeze mode or the moving image reproduction mode, the still image of the ultrasound image or the captured image stored by the image saving operation of the operator is read from the storage unit 26 and displayed on the display 13.

[Screen Saver Function and Automatic Freeze Function]

Similarly to the conventional ultrasound diagnostic apparatus, the ultrasound diagnostic apparatus 10 also has a screen saver function and an automatic freeze function (screen saver processing and freeze processing in the present invention). The screen saver function is a process of displaying, on the screen 13a, a predetermined image that hides information displayed on the screen 13a of the display 13. The automatic freeze function is processing for stopping transmission and reception of ultrasound waves in the ultrasound probe 12.

In the conventional ultrasound diagnostic apparatus, as described above, the screen saver function and the automatic freeze function are automatically activated when any one of the following conditions (1) to (3) is satisfied. (1) A non-operation time of a physical input device, for example, a button, a touch panel, a mouse, and the like passes a predetermined time. (2) A predetermined time during which the line of sight of the operator captured by the camera of the ultrasound diagnostic apparatus is not directed to the monitor screen passes. (3) A non-input time of the video to the camera of the ultrasound diagnostic apparatus passes for a predetermined time.

Meanwhile, in the ultrasound diagnostic apparatus, in the above-described live mode, in a case where a doctor performs puncture on a diagnosis site of a patient, there is a case where a needle to be punctured is positioned without moving the ultrasound probe. In this case, since the doctor performs puncture without operating the input device or directing the line of sight to the monitor screen, any one of the above conditions (1) to (3) may be satisfied. Therefore, contrary to the intention of the doctor, the above-described screen saver function and automatic freeze function are activated, and there is a problem that the ultrasound image cannot be checked when it is desired to check the ultrasound image.

In addition, in the moving image reproduction mode and the still image reproduction mode described above, a similar problem may occur also in a case where a doctor explains a symptom and the like to a patient while displaying a moving image or a still image on a monitor screen. For example, in a case where the doctor gives explanation without operating the input device or directing the line of sight to the monitor screen during reproduction of a moving image or a still image, any one of the above conditions (1) to (3) may be satisfied. Also in such a case, contrary to the intention of the doctor, the above-described screen saver function and automatic freeze function are activated, and there is a problem that the moving image and the still image cannot be checked when they are desired to check the ultrasound image.

Therefore, in the ultrasound diagnostic apparatus 10 according to the present embodiment, when the ultrasound image or the captured image is displayed on the display 13, the controller 21 determines whether or not at least one of the following non-operation determination conditions (A1) and (A2) is continuously satisfied for a predetermined time or more. Alternatively, when the ultrasound image or the captured image is displayed on the display 13, the controller 21 determines whether or not at least two of the following non-operation determination conditions (A1) to (A4) are continuously satisfied for a predetermined time or more.

Although described in detail below, the non-operation determination conditions (A1) to (A4) are conditions for determining that the operator is not in the operation state using non-contact detection for detecting the operation state of the operator in a non-contact manner, and are different conditions.

The non-operation determination conditions (A1) to (A4) are determined, for example, when the controller 21 displays an ultrasound image or a captured image on the display 13 in the above-described live mode, moving image reproduction mode, or still image reproduction mode. Then, in a case where at least one of the non-operation determination conditions (A1) and (A2) is satisfied continuously for a predetermined time or more, the controller 21 activates at least one of the screen saver function and the automatic freeze function. Alternatively, in a case where at least two of the non-operation determination conditions (A1) to (A4) are satisfied continuously for a predetermined time or more, the controller 21 may activate at least one of the screen saver function and the automatic freeze function.

The non-operation determination conditions (A1) to (A4) are as follows.

(A1) A state in which, in the input captured image, the change amount of the ultrasound probe 12 and surroundings of the ultrasound probe 12 is equal to or less than the first threshold value.

(A2) A state in which the volume of the input voice is equal to or less than the second threshold value, or a state in which the volume of the specific frequency of the input sound is equal to or less than the third threshold value.

(A3) A state in which the change amount of the ultrasound image is equal to or less than the fourth threshold value.

(A4) A state in which the operator is not facing the screen 13a of the display 13 in the input captured image.

The non-operation determination condition (A1) will be described. As described above, the first imager 15 is disposed to be able to image the ultrasound probe 12 and the surroundings (for example, the site of the subject, the puncture needle, the operator's hand, and the like), and the image captured by the first imager 15 is input to the controller 21 via the image acquisition unit 24.

The controller 21 performs predetermined image processing on the captured image (hereinafter, it may be referred to as a captured probe image) by the first imager 15 input via the image acquisition unit 24, and determines whether or not the change amount of the ultrasound probe 12 and the surroundings has become equal to or less than the first threshold value. That is, it is determined whether or not there is a change in the position of the ultrasound probe 12 or the surroundings.

The first threshold value is a threshold value for determining whether or not there is no change in the position of the ultrasound probe 12 or the surroundings. In a case where the change amount of the ultrasound probe 12 or the surroundings is equal to or less than the first threshold value, the controller 21 determines that the ultrasound probe 12 or the surroundings are not moving. On the other hand, in a case where the change amount of the ultrasound probe 12 or the surroundings is larger than the first threshold value, the controller 21 determines that the ultrasound probe 12 or the surroundings are moving.

Then, the controller 21 determines that the non-operation determination condition (A1) is satisfied when the change amount of the ultrasound probe 12 or the surroundings is equal to or less than the first threshold value.

The non-operation determination condition (A2) will be described. As described above, the sound inputter 17 acquires surrounding sound and generates sound data, and the sound data generated by the sound inputter 17 is input to the controller 21 via the sound acquisition unit 25.

The controller 21 performs predetermined data processing on the sound data input via the sound acquisition unit 25, extracts voice, and determines whether or not the volume of the voice has become equal to or less than the second threshold value. In addition, the controller 21 performs predetermined data processing on the sound data input via the sound acquisition unit 25, extracts sound of a specific frequency corresponding to the voice, and may determine whether or not the volume of the voice has become equal to or less than the third threshold value. That is, it is determined whether or not the operator is not around the ultrasound diagnostic apparatus 10.

The second threshold value and the third threshold value are threshold values for determining whether or not the operator is not around the ultrasound diagnostic apparatus 10. The controller 21 determines that the operator is not around the ultrasound diagnostic apparatus 10 in a case where the volume of the voice becomes equal to or less than the second threshold value or the volume of the specific frequency of the sound becomes equal to or less than the third threshold value. On the other hand, the controller 21 determines that the operator is around the ultrasound diagnostic apparatus 10 in a case where the volume of the voice becomes larger than the second threshold value or the volume of the specific frequency of the sound becomes larger than the third threshold value.

Then, the controller 21 determines that the non-operation determination condition (A2) is satisfied in a case where the volume of the voice becomes equal to or less than the second threshold value or the volume of the specific frequency of the sound becomes equal to or less than the third threshold value.

The non-operation determination condition (A3) will be described. As described above, the ultrasound image acquired using the ultrasound probe 12 and the like is input to the controller 21.

The controller 21 performs predetermined image processing on the input ultrasound image and determines whether or not the change amount of the ultrasound image is equal to or less than the fourth threshold value. That is, it is determined whether or not the operator is not using the ultrasound probe 12. For example, in a case where the operator returns the ultrasound probe 12 that is transmitting and receiving ultrasound waves to the probe holder, there is no change in the ultrasound image, and the change amount of the ultrasound image is equal to or less than the fourth threshold value. Therefore, it can be determined that the operator is not using the ultrasound probe 12.

The fourth threshold value is a threshold value for determining whether or not the position of the ultrasound probe 12 is not moving. In a case where the change amount of the ultrasound image is equal to or less than the fourth threshold value, the controller 21 determines that the ultrasound probe 12 is not moving. On the other hand, in a case where the change amount of the ultrasound image is larger than the fourth threshold value, the controller 21 determines that the ultrasound probe 12 is moving.

Then, the controller 21 determines that the non-operation determination condition (A3) is satisfied when the change amount of the ultrasound image is equal to or less than the fourth threshold value.

The non-operation determination condition (A4) will be described. As described above, the second imager 16 is disposed to be able to image the operator facing the screen 13a, and the image captured by the second imager 16 is input to the controller 21 via the image acquisition unit 24.

The controller 21 performs predetermined image processing on the captured image (hereinafter, it may be referred to as a captured operator image) by the second imager 16 input via the image acquisition unit 24, recognizes the face orientation and the line of sight of the operator, and determines whether or not the operator is facing the screen 13a.

For example, the controller 21 can recognize the face orientation and the line of sight of the operator in the captured operator image, and determines that the operator is facing the screen 13a when the face orientation and the line of sight is the direction of the screen 13a. In addition, for example, in a case where the operator is not illustrated in the captured operator image or the face orientation or the line of sight of the operator cannot be recognized in the captured operator image, the controller 21 determines that the operator is not facing the screen 13a.

Then, the controller 21 determines that the non-operation determination condition (A4) is satisfied when the operator is not facing the screen 13a.

In a case where the above determination is performed and at least one of the non-operation determination conditions (A1) and (A2) is satisfied continuously for a predetermined time or more, the controller 21 activates at least one of the screen saver function and the automatic freeze function. Alternatively, in a case where at least two of the non-operation determination conditions (A1) to (A4) are satisfied continuously for a predetermined time or more, the controller 21 activates at least one of the screen saver function and the automatic freeze function.

In this way, since it is difficult to activate the screen saver function and the automatic freeze function, it is possible to prevent the screen saver function and the automatic freeze function from being activated against the intention of the operator. In addition, since the screen saver function and the automatic freeze function can be prevented from being activated against the intention of the operator, the screen saver function and the automatic freeze function can be activated at an appropriate timing.

In addition, in a case where the remaining time until the predetermined time is equal to or less than the predetermined remaining time, the controller 21 may make at least one value of the first threshold value, the second threshold value, the third threshold value, and the fourth threshold value smaller than a value before the predetermined remaining time. For example, assuming that the predetermined time is 60 seconds and the predetermined remaining time is 10 seconds, the first threshold value during the passed time of 50 to 60 seconds in which the remaining time until the predetermined time (60 seconds) is equal to or less than the predetermined remaining time (10 seconds) is made smaller than the first threshold value during the passed time of 0 to 50 seconds. The same applies to the second threshold value, the third threshold value, and the fourth threshold value.

As described above, in a case where the remaining time until the predetermined time is equal to or less than the predetermined remaining time, the non-operation determination conditions (A1) to (A3) are made difficult to be satisfied by decreasing the threshold value, and the screen saver function and the automatic freeze function are not easily activated. Thus, it is possible to prevent the screen saver function and the automatic freeze function from being activated against the intention of the operator. Then, since the screen saver function and the automatic freeze function can be prevented from being activated against the intention of the operator, the screen saver function and the automatic freeze function can be activated at an appropriate timing.

On the other hand, the controller 21 determines the following processing end conditions (B1) to (B5), and ends the operation of at least one of the screen saver function and the automatic freeze function in a case where any one of the following processing end conditions (B1) to (B5) is satisfied.

(B1) A state in which, in the input captured image, the change amount of the ultrasound probe 12 and surroundings of the ultrasound probe 12 is larger than the first threshold value.

(B2) A state in which the volume of the input voice is larger than the second threshold value (or the volume of the specific frequency of the input sound is larger than the third threshold value).

(B3) A state in which the change amount of the ultrasound image is larger than the fourth threshold value.

(B4) A state in which the operator is facing the screen 13*a* of the display 13 in the input captured image.

(B5) A state in which there is an operation input.

The processing end conditions (B1) to (B4) are basically in a front back relationship with the non-operation determination conditions (A1) to (A4) described above.

For example, under the non-operation determination condition (A1), the controller 21 determines whether the change amount of the ultrasound probe 12 or the surroundings is equal to or less than the first threshold value, and under the processing end condition (B1), the controller 21 determines that the change amount of the ultrasound probe 12 or the surroundings is larger than the first threshold value. Here, the non-operation determination condition (A1) is set to be equal to or less than the first threshold value, and the processing end condition (B1) is set to be larger than the first threshold value. However, the non-operation determination condition (A1) may be set to be less than the first threshold value, and the processing end condition (B1) may be set to be equal to or larger than the first threshold value.

In addition, in the non-operation determination condition (A2), the controller 21 determines whether the volume of the voice has become equal to or less than the second threshold value or the volume of the specific frequency of the sound has become equal to or less than the third threshold value. On the other hand, in the processing end condition (B2), it is determined that the volume of the voice is larger than the second threshold value or that the volume of the specific frequency of the sound is larger than the third threshold value. Here, the non-operation determination condition (A2) is set to be equal to or less than the second threshold value, and the processing end condition (B2) is set to be larger than the second threshold value. However, the non-operation determination condition (A2) may be set to be less than the second threshold value, and the processing end condition (B2) may be set to be equal to or larger than the second threshold value. The same applies to the third threshold value.

In addition, under the non-operation determination condition (A3), the controller 21 determines whether the change amount of the ultrasound image is equal to or less than the fourth threshold value, and under the processing end condition (B3), the controller 21 determines that the change amount of the ultrasound image is larger than the fourth threshold value. Here, the non-operation determination condition (A3) is set to be equal to or less than the fourth threshold value, and the processing end condition (B3) is set to be larger than the fourth threshold value. However, the non-operation determination condition (A3) may be set to be less than the fourth threshold value, and the processing end condition (B3) may be set to be equal to or larger than the fourth threshold value.

In addition, the controller 21 determines whether the operator is not facing the screen 13*a* under the non-operation determination condition (A4), and determines that the operator is facing the screen 13*a* under the processing end condition (B4).

The processing end condition (B5) will be described. As described above, the input operation performed by the operator on the operation input unit 14 is converted into an operation signal and input to the controller 21.

The controller 21 determines whether or not there is an operation input based on the presence or absence of an operation signal from the operation input unit 14. Then, when there is an operation signal from the operation input unit 14, the controller 21 determines that the processing end condition (B5) is satisfied.

The controller 21 determines the processing end conditions (B1) to (B5) as described above, and ends the operation of at least one of the screen saver function and the automatic freeze function in a case where any one of the following processing end conditions (B1) to (B5) is satisfied.

As described above, in the present embodiment, in a case where at least one of the non-operation determination conditions (A1) and (A2) is satisfied continuously for a predetermined time or more, the ultrasound diagnostic apparatus 10 activates at least one of the screen saver function and the automatic freeze function. Alternatively, in a case where at least two of the non-operation determination conditions (A1) to (A4) are satisfied continuously for a predetermined time or more, the ultrasound diagnostic apparatus 10 activates at least one of the screen saver function and the automatic freeze function.

In this way, the screen saver function and the automatic freeze function are made difficult to be activated. Therefore, it is possible to prevent the screen saver function and the automatic freeze function from being activated against the intention of the operator.

For example, in the live mode, even in a state where the operator is performing puncture and does not perform other operations, it is possible to prevent the screen saver function and the automatic freeze function from being activated against the intention of the operator. In addition, in the moving image reproduction mode, even in a state where the operation of the ultrasound diagnostic apparatus 10 is not performed during the explanation to the patient and the like, it is possible to prevent the screen saver function and the automatic freeze function from being activated against the intention of the operator. The same applies to the still image reproduction mode.

In addition, the screen saver function and the automatic freeze function are stopped when any one of the processing end conditions (B1) to (B5) is satisfied. Therefore, in response to the operator's operation on the ultrasound diagnostic apparatus 10, the screen saver function and the automatic freeze function can be stopped according to the operator's intention.

As described above, the activation of the screen saver function and the automatic freeze function is less likely to satisfy the conditions compared with the processing end condition. Therefore, it is possible to prevent the screen saver function and the automatic freeze function from being activated against the intention of the operator.

Note that in a case where the activation of the screen saver function and the automatic freeze function cannot be permitted, the activation of the screen saver function and the automatic freeze function may be prohibited.

For example, in a case where a doctor who is an operator performs puncture on a patient who is a subject while checking an ultrasound image, when the screen saver function and the automatic freeze function are activated, the doctor cannot check the ultrasound image. In such a case, since the activation of the screen saver function and the automatic freeze function cannot be permitted, the activation of the screen saver function and the automatic freeze function is prohibited.

For example, treatment such as puncture using the ultrasound diagnostic apparatus 10 is performed without performing patient registration on the ultrasound diagnostic apparatus 10. Therefore, the controller 21 can determine whether or not it is a treatment such as puncture depending on the presence or absence of patient information (display content in the present invention) displayed on the screen 13a of the display 13. In a case where there is no patient information to be displayed on the screen 13a, the controller 21 determines that the use state of the ultrasound diagnostic apparatus 10 is treatment. In this case, the controller 21 determines that the activation of the screen saver function and the automatic freeze function cannot be permitted, and prohibits the activation of the screen saver function and the automatic freeze function.

On the other hand, in a case where there is patient information to be displayed on the screen 13a, the controller 21 determines that the use state of the ultrasound diagnostic apparatus 10 is not a treatment such as puncture but diagnosis. In this case, the controller 21 determines that the activation of the screen saver function and the automatic freeze function can be permitted, and permits the activation of the screen saver function and the automatic freeze function.

In addition, in a treatment such as puncture using the ultrasound diagnostic apparatus 10, an image in a B (Brightness) mode (referred to as a B mode image) as a tomographic image is displayed as an ultrasound image to be displayed on the screen 13a. Therefore, the controller 21 can determine whether or not it is a treatment such as puncture based on the image mode of the ultrasound image (display content in the present invention) displayed on the screen 13a. In a case where the ultrasound image displayed on the screen 13a is the B mode image, the controller 21 determines that the use state of the ultrasound diagnostic apparatus 10 is treatment. In this case, the controller 21 determines that the activation of the screen saver function and the automatic freeze function cannot be permitted, and prohibits the activation of the screen saver function and the automatic freeze function.

On the other hand, in a case where the ultrasound image displayed on the screen 13a is an image other than the B mode image (for example, a pulse Doppler image, a color Doppler image, and the like), the controller 21 determines that the use state of the ultrasound diagnostic apparatus 10 is diagnosis instead of a treatment such as puncture. In this case, the controller 21 determines that the activation of the screen saver function and the automatic freeze function can be permitted, and permits the activation of the screen saver function and the automatic freeze function.

In addition, the controller 21 may determine the use state (treatment or diagnosis) of the ultrasound diagnostic apparatus 10 by combining the state of the patient information described above and the state of the image mode of the ultrasound image, and prohibit or permit activation of the screen saver function and the automatic freeze function.

In addition, the controller 21 may change the difficulty of activation (easiness of activation) of the screen saver function and the automatic freeze function by changing a condition related to a non-operation determination condition instead of prohibition and permission of activation of the screen saver function and the automatic freeze function.

For example, as described above, in a case where there is no patient information to be displayed on the screen 13a, the controller 21 makes it difficult to satisfy the non-operation determination conditions (A1) to (A3) by decreasing the first to fourth threshold values in the non-operation determination conditions (A1) to (A3). In addition, the controller 21 may activate the screen saver function and the automatic freeze function in a case where many of the non-operation determination conditions (A1) to (A4) (for example, two or more conditions) are satisfied continuously for a predetermined time or more. This makes it difficult to activate the screen saver function and the automatic freeze function.

On the other hand, in a case where there is patient information to be displayed on the screen 13a, the controller 21 makes it easy to satisfy the non-operation determination conditions (A1) to (A3) by increasing the first to fourth threshold values in the non-operation determination conditions (A1) to (A3). In addition, the controller 21 may activate the screen saver function and the automatic freeze function in a case where a little condition of the non-operation determination conditions (A1) to (A4) (for example, one condition) is satisfied continuously for a predetermined time or more. This makes it easy to activate the screen saver function and the automatic freeze function.

Similarly, the first to fourth threshold values may be changed or the number of non-operation determination conditions to be satisfied continuously for a predetermined time or more may be changed based on the state of the image mode of the ultrasound image described above or based on a combination of the state of the patient information and the state of the image mode of the ultrasound image described above. In this way, the difficulty of activation (easiness of activation) of the screen saver function and the automatic freeze function is changed.

[Method for Controlling Ultrasound Diagnostic Apparatus, and Control Program of Ultrasound Diagnostic Apparatus]

Figure 3:
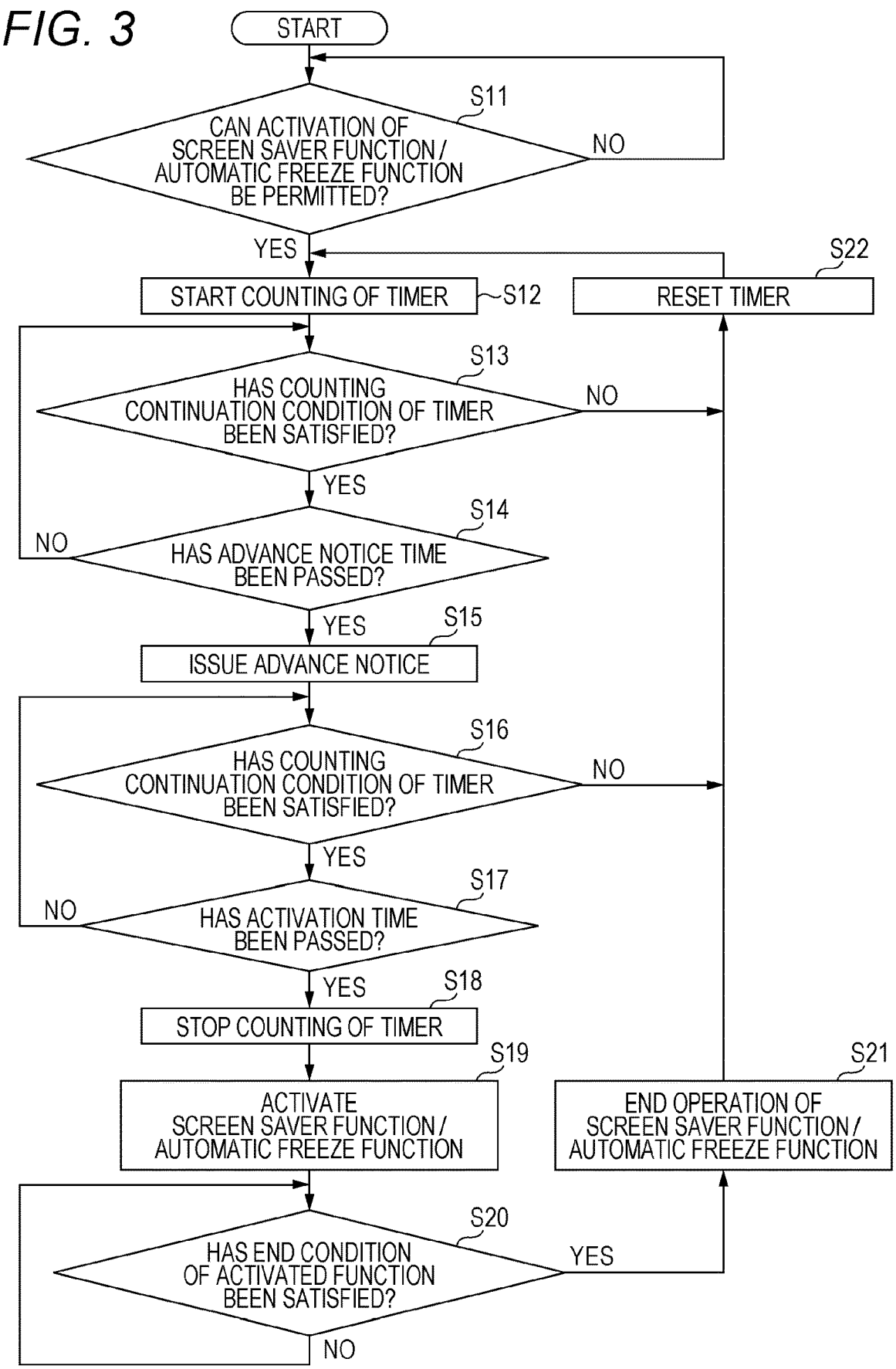
FIG. 3 is a flowchart illustrating a method for controlling the ultrasound diagnostic apparatus according to the embodiment of the present invention.

FIG. 3 is a flowchart illustrating a method for controlling the ultrasound diagnostic apparatus according to the embodiment. Each step illustrated in FIG. 3 and FIGS. 4 to 5 to be described later is executed, for example, by the controller 21 of the ultrasound diagnostic apparatus 10 according to a program.

In the ultrasound diagnostic apparatus 10, the operator turns on the power, and in response to the subsequent operation input, for example, the live mode, the moving image reproduction mode, the still image reproduction mode, and the like is selected, and the following steps S11 to S22 are executed.

For example, in a case where the live mode is selected, the ultrasound image or the captured image is displayed on the screen 13a of the display 13 as described above. In the live mode, for example, in a case where puncture is performed, a B mode image is displayed as an ultrasound image. In such a state, the following steps S11 to S22 are executed.

(Step S11)

The controller 21 determines whether or not activation of the screen saver function and the automatic freeze function can be permitted. In a case where it is in a permissive state (YES), the process proceeds to step S12. In a case where it is in a non-permissive state (NO), step S11 is repeated until it becomes a permissive state.

For example, as described above, in a case of a treatment in which where a doctor who is an operator performs puncture on a patient who is a subject while checking an ultrasound image, activation of the screen saver function and the automatic freeze function cannot be permitted. Therefore, by repeating step S11, the process is prohibited from proceeding to the following step S19, and the activation of the screen saver function and the automatic freeze function is substantially prohibited.

Note that, although not illustrated in the flowchart illustrated in FIG. 3, instead of repeating step S11, in the following steps S12 to S18, counting by the timer may not be performed, and the process may be prohibited from proceeding to step S19.

Similarly, although not illustrated in the flowcharts illustrated in FIGS. 3 and 4, in the following steps S13 and S16, even if the timer counting continuation condition is satisfied, the process may proceed to step S22 on the assumption that the timer counting continuation condition is not satisfied, and the process may be prohibited from proceeding to step S19.

In addition, instead of step S11, the state of the patient information or the state of the image mode of the ultrasound image may be determined, and the first to fourth threshold values may be changed or the number of non-operation determination conditions to be satisfied continuously for a predetermined time or more may be changed based on the determination. In addition, the following steps S12 to S22 may be executed without executing step S11.

(Step S12)

The controller 21 starts counting of the timer.

(Step S13)

The controller 21 determines whether or not a counting continuation condition of the timer is satisfied. In a case where the timer counting continuation condition is satisfied (YES), the process proceeds to step S14, and in a case where the timer counting continuation condition is not satisfied (NO), the process proceeds to step S22.

Determination as to whether or not the counting continuation condition of the timer is satisfied will be described with reference to FIG. 4. FIG. 4 is a flowchart illustrating determination of a counting continuation condition of a timer in the flowchart illustrated in FIG. 3.

(Step S13-1)

The controller 21 determines whether or not the operator is not facing the screen 13a in the captured image from the second imager 16 and the like. This is the above-described non-operation determination condition (A4). Then, as described above, the controller 21 performs predetermined image processing on the captured image (captured operator image), recognizes the face orientation and the line of sight of the operator, and determines whether or not the operator is facing the screen 13a. In a case where the operator is not facing the screen 13a (YES), the process proceeds to step S13-2, and in a case where the operator is facing the screen 13a (NO), the process proceeds to step S22.

(Step S13-2)

In the captured image from the first imager 15 and the like, the controller 21 determines whether or not the change amount of the ultrasound probe 12 or the surroundings is equal to or less than the first threshold value. This is the above-described non-operation determination condition (A1). Then, as described above, the controller 21 performs predetermined image processing on the captured image (captured probe image), and determines whether or not the change amount of the ultrasound probe 12 or the surroundings has become equal to or less than the first threshold value. In a case where the change amount of the ultrasound probe 12 or the surroundings is equal to or less than the first threshold value (YES), the process proceeds to step S13-3, and in a case where the change amount of the ultrasound probe 12 or the surroundings is larger than the first threshold value (NO), the process proceeds to step S22.

(Step S13-3)

In the sound data from the sound inputter 17 and the like, the controller 21 determines whether or not the volume of the voice has become equal to or less than the second threshold value or whether or not the volume of the specific frequency of the sound has become equal to or less than the third threshold value. This is the above-described non-operation determination condition (A2). Then, as described above, the controller 21 performs predetermined data processing on the sound data to extract a voice or a sound having the specific frequency corresponding to the voice, and determines whether or not the volume of the voice has become equal to or less than the second threshold value or the volume of the sound at the specific frequency has become equal to or less than the third threshold value. In a case where the volume of the voice is equal to or less than the second threshold value or in a case where the volume of the specific frequency of the sound is equal to or less than the third threshold value (YES), the process proceeds to step S13-4, and in a case where the volume of the voice is larger than the second threshold value or in a case where the volume of the specific frequency of the sound is larger than the third threshold value (NO), the process proceeds to step S22.

(Step S13-4)

In the ultrasound image from the ultrasound probe 12 and the like, the controller 21 determines whether or not the change amount of the ultrasound image is equal to or less than the fourth threshold value. This is the above-described non-operation determination condition (A3). Then, as described above, the controller 21 perform predetermined image processing on the ultrasound image and determines whether or not the change amount of the ultrasound image is equal to or less than the fourth threshold value. In a case where the change amount of the ultrasound image is equal to or less than the fourth threshold value (YES), the process proceeds to step S14, and in a case where the change amount of the ultrasound image is larger than the fourth threshold value (NO), the process proceeds to step S22.

In this manner, in step S12, the non-operation determination conditions (A1) to (A4) are determined, and in a case where the non-operation determination conditions (A1) to (A4) are satisfied, the process proceeds to the next step S14 to advance the timer counting.

Note that, here, all the non-operation determination conditions (A1) to (A4) are determined, and in a case where all the non-operation determination conditions (A1) to (A4) are satisfied, the timer counting is advanced. It is not limited to this, and for example, one of the non-operation determination conditions (A1) and (A2) may be determined, and in a case where the determined one non-operation determination condition is satisfied, the timer counting may be advanced. In addition, for example, two (or three) of the non-operation determination conditions (A1) to (A4) may be determined, and in a case where all of the determined two (or three) non-operation determination conditions are satisfied, the timer counting may be advanced.

Returning to FIG. 3, steps S14 and S15 will be described.
(Step S14)

The controller 21 checks whether or not the timer count has passed the advance notice time. In a case where the advance notice time has passed (YES), the process proceeds to step S15. On the other hand, in a case where the advance notice time has not passed (NO), the process returns to step S13. That is, step S13 is repeated until the advance notice time passes. When any one of the non-operation determination conditions (A1) to (A4) is not satisfied while step S13 is repeated, the process proceeds to step S22.

The advance notice time is set to a time before the activation time when the screen saver function and the automatic freeze function are activated, and has a meaning as a grace time until the screen saver function and the automatic freeze function are activated.

Here, the activation time is a time when the predetermined time has passed since the timer started counting. As an example, when the predetermined time is set to 60 seconds, the activation time is a time when 60 seconds have passed since the timer started counting. Then, when the advance notice time is set to 10 seconds before the activation time, the advance notice time is a time when 50 seconds have passed since the timer started to count, and when the timer count has passed 50 seconds, the process proceeds to step S15.
(Step S15)

The controller 21 issues the advance notice. As the advance notice, for example, the controller 21 may issue notice by sound using a speaker (not illustrated) included in the ultrasound diagnostic apparatus 10, or issue notice by screen display using the screen 13a of the display 13. As the advance notice by the screen display, for example, the controller 21 may display the remaining time until the activation time, display a preliminary announcement of activation of the screen saver function and the automatic freeze function by a message, or gradually darken the screen.
(Step S16)

The controller 21 determines whether or not a counting continuation condition of the timer is satisfied. In a case where the timer counting continuation condition is satisfied (YES), the process proceeds to step S17, and in a case where the timer counting continuation condition is not satisfied (NO), the process proceeds to step S22.

In step S16, the determination as to whether or not the counting continuation condition of the timer is satisfied is the same as that in step S13 (steps S13-1 to S13-4) described with reference to FIG. 4, and thus, the detailed description of step S16 is omitted here.

Then, also in step S16, similarly to step S13, the non-operation determination conditions (A1) to (A4) are determined, and in a case where the non-operation determination conditions (A1) to (A4) are satisfied, the process proceeds to the next step S17 to further advance the timer counting.

Note that, in step S16, the controller 21 may set at least one of the first threshold value, the second threshold value, the third threshold value, and the fourth threshold value to be smaller than the value in step S13. As described above, in a case where the remaining time until the activation time is equal to or less than the predetermined remaining time, the non-operation determination conditions (A1) to (A4) are made difficult to be satisfied by decreasing the threshold value, and the screen saver function and the automatic freeze function are not easily activated. Thus, it is possible to prevent the screen saver function and the automatic freeze function from being activated against the intention of the operator.

In addition, here, the value of the threshold value is changed with the difference of the advance notice time with respect to the activation time as the predetermined remaining time, but the predetermined remaining time is not limited to this, and may be set to a time immediately before the activation time, for example, 5 seconds before the activation time.
(Step S17)

The controller 21 checks whether or not the timer count has passed the activation time. In a case where the activation time has passed (YES), the process proceeds to step S18. On the other hand, in a case where the activation time has not passed (NO), the process returns to step S16. That is, step S16 is repeated until the activation time passes.

When any one of the non-operation determination conditions (A1) to (A4) is not satisfied while step S16 is repeated, the process proceeds to step S22. In a case where the operator desires to reset the count of the timer, for example, the operator moves the ultrasound probe 12 illustrated in the first imager 15, gives a voice, moves the ultrasound probe 12 to change the ultrasound image, or turns the face toward the second imager 16 after the above advance notice. By doing so intentionally, any one of the non-operation determination conditions (A1) to (A4) is not satisfied, and the process proceeds to step S22.
(Step S18)

The controller 21 stops counting of the timer.
(Step S19)

The controller 21 activates at least one of the screen saver function and the automatic freeze function. In this manner, the screen saver function and the automatic freeze function are activated when the non-operation determination conditions (A1) to (A4) are satisfied.
(Step S20)

The controller 21 determines whether or not the end condition of the activated screen saver function and automatic freeze function is satisfied. In a case where the end condition is satisfied (YES), the process proceeds to step S21, and in a case where the end condition is not satisfied (NO), step S20 is repeated until the end condition is satisfied.

The determination of whether or not the end condition of the activated screen saver function and the automatic freeze function is satisfied will be described with reference to FIG.

5. FIG. 5 is a flowchart illustrating determination of an end condition of an activated function in the flowchart illustrated in FIG. 3.
(Step S20-1)

The controller 21 determines whether or not there is an operation input based on the presence or absence of an operation signal from the operation input unit 14. This is the condition of the above-described processing end condition (B5). In a case where there is an operation input (YES), the process proceeds to step S21, and in a case where there is no operation input (NO), the process proceeds to step S20-2.
(Step S20-2)

The controller 21 determines whether or not the operator is facing the screen 13a in the captured operator image from the second imager 16 and the like. This is the condition of the above-described processing end condition (B4). Whether or not the operator is facing the screen 13a is determined by the method described in the non-operation determination condition (A4). In a case where the operator is facing the screen 13a (YES), the process proceeds to step S21, and in a case where the operator is not facing the screen 13a (NO), the process proceeds to step S20-3.
(Step S20-3)

In the captured probe image from the first imager 15 and the like, the controller 21 determines whether or not the change amount of the ultrasound probe 12 or the surroundings is larger than the first threshold value. This is the condition of the above-described processing end condition (B1). Whether or not the change amount of the ultrasound probe 12 or the surroundings is larger than the first threshold value is determined by the method described in the non-operation determination condition (A1). In a case where the change amount of the ultrasound probe 12 or the surroundings is larger than the first threshold value (YES), the process proceeds to step S21, and in a case where the change amount of the ultrasound probe 12 or the surroundings is equal to or less than the first threshold value (NO), the process proceeds to step S20-4.
(Step S20-4)

In the sound data from the sound inputter 17 and the like, the controller 21 determines whether or not the volume of the voice is larger than the second threshold value or whether or not the volume of the specific frequency of the sound is larger than the third threshold value. This is the condition of the above-described processing end condition (B2). Whether or not the volume of the voice is larger than the second threshold value or whether or not the volume of the specific frequency of the sound is larger than the third threshold value is determined by the method described in the non-operation determination condition (A2). In a case where the volume of the voice is larger than the second threshold value or in a case where the volume of the specific frequency of the sound is larger than the third threshold value (YES), the process proceeds to step S21, and in a case where the volume of the voice is equal to or less than the second threshold value or in a case where the volume of specific frequency of the sound is equal to or larger than the third threshold value (NO), the process proceeds to step S20-5.
(Step S20-5)

In the ultrasound image from the ultrasound probe 12 and the like, the controller 21 determines whether or not the change amount of the ultrasound image is larger than the fourth threshold value. This is the condition of the above-described processing end condition (B3). Whether or not the change amount of the ultrasound image is larger than the fourth threshold value is determined by the method described in the non-operation determination condition (A3). In a case where the change amount of the ultrasound image is larger than the fourth threshold value (YES), the process proceeds to step S21, and in a case where the change amount of the ultrasound image is equal to or less than the fourth threshold value (NO), the process proceeds to step S20-1.

As described above, in step S20, the processing end conditions (B1) to (B5) are determined, and when any one of the processing end conditions (B1) to (B5) is satisfied, the process proceeds to the next step S21. Thereafter, as described below, the operations of the screen saver function and the automatic freeze function are ended.

Returning to FIG. 3, steps S21 and S22 will be described.
(Step S21)

The controller 21 ends the operation of at least one of the screen saver function and the automatic freeze function, and proceeds to step S22. For example, the screen saver function automatically ends the operation, but the automatic freeze function may end the operation, which means that the automatic freeze function may restart the transmission and reception of the ultrasound wave, for example, in a case where the operator performs an input operation of recognizing the operation end after the controller 21 requests the operator to check the operation end.
(Step S22)

The controller 21 resets the timer and returns to step S12.

As described above, in the present embodiment, in a case where at least one of the non-operation determination conditions (A1) and (A2) is satisfied continuously for a predetermined time or more, the ultrasound diagnostic apparatus 10 activates at least one of the screen saver function and the automatic freeze function. Alternatively, in a case where at least two of the non-operation determination conditions (A1) to (A4) are satisfied continuously for a predetermined time or more, the ultrasound diagnostic apparatus 10 activates at least one of the screen saver function and the automatic freeze function.

Therefore, the screen saver function and the automatic freeze function are made difficult to be activated, and it is possible to prevent the screen saver function and the automatic freeze function from being activated against the intention of the operator. Then, since the screen saver function and the automatic freeze function can be prevented from being activated against the intention of the operator, the screen saver function and the automatic freeze function can be activated at an appropriate timing.

In addition, in the present embodiment, when any one of the processing end conditions (B1) to (B5) is satisfied, the ultrasound diagnostic apparatus 10 stops the activated screen saver function and automatic freeze function. Therefore, in response to the operator's operation on the ultrasound diagnostic apparatus 10, the screen saver function and the automatic freeze function can be stopped according to the operator's intention.

Although embodiments of the present invention have been described and illustrated in detail, the disclosed embodiments are made for purposes of illustration and example only and not limitation. The scope of the present invention should be interpreted by terms of the appended claims That is, the present invention can be implemented in various forms without departing from the gist or main features.

What is claimed is:
1. An ultrasound diagnostic apparatus comprising:
an ultrasound probe that transmits an ultrasound wave and receives a reflected wave of the ultrasound wave;

a display that displays an ultrasound image based on the reflected wave on a screen; and a hardware processor that activates at least one of a screen saver processing of displaying, on the screen, a predetermined image hiding information displayed on the screen and a freeze processing of stopping transmission and reception of the ultrasound wave by the ultrasound probe in a case where at least one of following non-operation determination conditions (A1) and (A2) is continuously satisfied for a predetermined time or more while the ultrasound image is displayed on the screen, wherein the non-operation determination conditions (A1) and (A2) are:

(A1) a state in which, in an input captured image, a change amount of the ultrasound probe and surroundings of the ultrasound probe is equal to or less than a first threshold value; and (A2) a state in which a volume of input voice is equal to or less than a second threshold value, or a state in which a volume of a specific frequency of input sound is equal to or less than a third threshold value.

2. The ultrasound diagnostic apparatus according to claim 1, wherein the hardware processor activates at least one of the screen saver processing and the freeze processing in a case where at least two of the non-operation determination conditions (A1) and (A2) and following non-operation determination conditions (A3) and (A4) are continuously satisfied for a predetermined time or more, and the non-operation determination conditions (A3) and (A4) are:

(A3) a state in which a change amount of the ultrasound image is equal to or less than a fourth threshold value; and (A4) a state in which an operator is not facing the screen in an input captured image.

3. The ultrasound diagnostic apparatus according to claim 1, wherein the hardware processor determines whether a use state of the ultrasound diagnostic apparatus is diagnosis or treatment based on display content displayed on the screen, and prohibits activation of the screen saver processing and the freeze processing in a case where it is determined that the use state is the treatment.

4. The ultrasound diagnostic apparatus according to claim 1, wherein the hardware processor determines whether a use state of the ultrasound diagnostic apparatus is diagnosis or treatment based on display content displayed on the screen, and changes a condition related to the non-operation determination condition depending on whether the use state is the diagnosis or the treatment.

5. The ultrasound diagnostic apparatus according to claim 2, wherein the hardware processor determines whether a use state of the ultrasound diagnostic apparatus is diagnosis or treatment based on display content displayed on the screen, and in a case where it is determined that the use state is the treatment, the hardware processor makes at least one value of the first threshold value, the second threshold value, the third threshold value, and the fourth threshold value smaller than a value in a case where it is determined that the use state is the diagnosis.

6. The ultrasound diagnostic apparatus according to claim 2, wherein the hardware processor makes at least one of the first threshold value, the second threshold value, the third threshold value, and the fourth threshold value smaller than a value before a predetermined remaining time in a case where a remaining time until the predetermined time is equal to or less than the predetermined remaining time.

7. The ultrasound diagnostic apparatus according to claim 1, wherein the hardware processor activates a timer that counts the predetermined time when at least one of the non-operation determination conditions (A1) and (A2) is satisfied, and displays the remaining time on the screen in a case where the remaining time until the predetermined time is equal to or less than a predetermined remaining time.

8. The ultrasound diagnostic apparatus according to claim 2, wherein the hardware processor activates a timer that counts the predetermined time when at least two of the non-operation determination conditions (A1) to (A4) are satisfied, and displays the remaining time on the screen in a case where the remaining time until the predetermined time is equal to or less than a predetermined remaining time.

9. The ultrasound diagnostic apparatus according to claim 2, wherein in a case where any one of following processing end conditions (B1) to (B5) is satisfied, the hardware processor ends at least one of the screen saver processing and the freeze processing, and the processing end conditions (B1) to (B5) are:

(B1) a state in which, in the input captured image, a change amount of the ultrasound probe and surroundings of the ultrasound probe is larger than the first threshold value;

(B2) a state in which the volume of the input voice is larger than the second threshold value or the volume of the specific frequency of the input sound is larger than the third threshold value;

(B3) a state in which the change amount of the ultrasound image is larger than a fourth threshold value;

(B4) a state in which the operator is facing the screen in the input captured image; and (B5) a state in which there is an operation input.

10. The ultrasound diagnostic apparatus according to claim 8, wherein in a case where any one of following processing end conditions (B1) to (B5) is satisfied, the hardware processor stops counting of the timer, resets the timer, and ends at least one of the screen saver processing and the freeze processing, and the processing end conditions (B1) to (B5) are:

(B1) a state in which, in the input captured image, a change amount of the ultrasound probe and surroundings of the ultrasound probe is larger than the first threshold value;

(B2) a state in which the volume of the input voice is larger than the second threshold value or the volume of the specific frequency of the input sound is larger than the third threshold value;

(B3) a state in which the change amount of the ultrasound image is larger than a fourth threshold value;

(B4) a state in which the operator is facing the screen in the input captured image; and (B5) a state in which there is an operation input.

11. The ultrasound diagnostic apparatus according to claim 1, comprising:
a first imager that captures an image of the ultrasound probe and surroundings of the ultrasound probe.

12. The ultrasound diagnostic apparatus according to claim 11, wherein
the hardware processor determines whether or not a change amount of the ultrasound probe and the surroundings of the ultrasound probe is equal to or less than the first threshold value based on images of the ultrasound probe and the surroundings of the ultrasound probe captured by the first imager.

13. The ultrasound diagnostic apparatus according to claim 2, comprising:
a second imager that images the operator.

14. The ultrasound diagnostic apparatus according to claim 13, wherein
the hardware processor determines whether or not the operator faces the screen based on an image of the operator captured by the second imager.

15. The ultrasound diagnostic apparatus according to claim 1, comprising
a sound inputter to which the voice or the sound is input.

16. The ultrasound diagnostic apparatus according to claim 15, wherein
the hardware processor determines whether or not the volume of the voice is equal to or less than the second threshold value or whether or not the volume of the specific frequency of the sound is equal to or less than the third threshold value based on the voice or the sound input to the sound inputter.

17. The ultrasound diagnostic apparatus according to claim 2, wherein
the hardware processor determines whether or not a change amount of the ultrasound image is equal to or less than the fourth threshold value based on the ultrasound image acquired by the ultrasound probe.

18. A method for controlling an ultrasound diagnostic apparatus, the method comprising:
transmitting an ultrasound wave and receiving a reflected wave of the ultrasound wave by an ultrasound probe, and activating at least one of a screen saver processing of displaying, on the screen, a predetermined image hiding information displayed on the screen and a freeze processing of stopping transmission and reception of the ultrasound wave by the ultrasound probe in a case where at least one of following non-operation determination conditions (A1) and (A2) is continuously satisfied for a predetermined time or more while the ultrasound image based on the reflected wave is displayed on the screen, wherein
the non-operation determination conditions (A1) and (A2) are:
(A1) a state in which, in an input captured image, a change amount of the ultrasound probe and surroundings of the ultrasound probe is equal to or less than a first threshold value; and
(A2) a state in which a volume of input voice is equal to or less than a second threshold value, or a state in which a volume of a specific frequency of input sound is equal to or less than a third threshold value.

19. A non-transitory recording medium storing a computer readable control program of an ultrasound diagnostic apparatus, causing a computer to perform:
transmitting an ultrasound wave and receiving a reflected wave of the ultrasound wave by using an ultrasound probe, and activating at least one of a screen saver processing of displaying, on the screen, a predetermined image hiding information displayed on the screen and a freeze processing of stopping transmission and reception of the ultrasound wave by the ultrasound probe in a case where at least one of following non-operation determination conditions (A1) and (A2) is continuously satisfied for a predetermined time or more while the ultrasound image based on the reflected wave is displayed on the screen, wherein
the non-operation determination conditions (A1) and (A2) are:
(A1) a state in which, in an input captured image, a change amount of the ultrasound probe and surroundings of the ultrasound probe is equal to or less than a first threshold value, and
(A2) a state in which a volume of input voice is equal to or less than a second threshold value, or a state in which a volume of a specific frequency of input sound is equal to or less than a third threshold value.

* * * * *